US010598673B2

(12) United States Patent
Maas et al.

(10) Patent No.: US 10,598,673 B2
(45) Date of Patent: Mar. 24, 2020

(54) CONTAINER COMPRISING HAEMOGLOBIN FRACTIONS

(71) Applicant: EUROTROL B.V., Ede (NL)

(72) Inventors: Bartholomeus Henricus Antonius Maas, Ede (NL); Carolina Johanna Huizing, Ede (NL)

(73) Assignee: EUROTROL B.V., Ede (NL)

( * ) Notice: Subject to any disclaimer, the term of this patent is extended or adjusted under 35 U.S.C. 154(b) by 281 days.

(21) Appl. No.: 15/536,958

(22) PCT Filed: Dec. 10, 2015

(86) PCT No.: PCT/EP2015/079294
§ 371 (c)(1),
(2) Date: Jun. 16, 2017

(87) PCT Pub. No.: WO2016/102196
PCT Pub. Date: Jun. 30, 2016

(65) Prior Publication Data
US 2017/0350905 A1    Dec. 7, 2017

(30) Foreign Application Priority Data

Dec. 22, 2014 (EP) .................................. 14199807

(51) Int. Cl.
*G01N 33/72* (2006.01)
*G01N 33/49* (2006.01)

(52) U.S. Cl.
CPC ........... *G01N 33/726* (2013.01); *G01N 33/49* (2013.01); *G01N 33/4925* (2013.01); *G01N 33/721* (2013.01); *G01N 33/728* (2013.01); *G01N 2333/745* (2013.01); *G01N 2333/805* (2013.01)

(58) Field of Classification Search
CPC .. G01N 33/726; G01N 33/4925; G01N 33/49; G01N 33/721; G01N 33/728;
(Continued)

(56) References Cited

U.S. PATENT DOCUMENTS 5,759,370 A * 6/1998 Pawliszyn ........ G01N 27/44795
204/451
5,759,774 A * 6/1998 Hackett .................. A61K 35/18
435/2
(Continued)

FOREIGN PATENT DOCUMENTS

| EP | 0 181 033 A1 | 5/1986 |
|---|---|---|
| GB | 2 308 444 A | 6/1997 |
| WO | 2011/093697 A1 | 8/2011 |
| WO | 2014/142655 A1 | 9/2014 |

OTHER PUBLICATIONS

Maas et al., "Lyophilized bovine hemoglobin as a possible reference material for the determination of hemoglobin derivatives in human blood," Clinical Chemistry 44:11, 2331-2339 (1998).
(Continued)

*Primary Examiner* — Lore R Jarrett
(74) *Attorney, Agent, or Firm* — Volpe and Koenig, P.C.

(57) ABSTRACT

The present invention relates to a container comprising haemoglobin fractions, wherein said container comprising at least two compartments, wherein a first compartment comprises O2Hb (oxyhaemoglobin) and a second compartment comprises MetHb (methaemoglobin), optionally wherein O2Hb is stabilized. The invention also relates to a kit for determining the reliability of a CO-oximetry device, wherein said kit comprises said container and to a method for determining the reliability of a CO-oximetry device using said container.

15 Claims, 1 Drawing Sheet

(58) Field of Classification Search
CPC ....... G01N 2333/805; G01N 2333/745; G01N 33/70; G01N 2496/00; B65D 51/002; B65D 33/02; B65D 31/04; B65D 75/26; B01L 3/523; B01L 3/505; B01L 2300/0887; B01L 2300/044; B01L 2200/16; B01L 2200/12; B01L 2300/123; B32B 27/40; B32B 27/365; B32B 27/34; B32B 27/32; B32B 27/08; B32B 2439/80; B32B 2439/46; B32B 2307/732; B32B 2307/7244; B32B 2307/7242; B32B 2307/518; B32B 2255/20; B32B 2255/10
See application file for complete search history.

(56) References Cited

U.S. PATENT DOCUMENTS

| | | | | |
|---|---|---|---|---|
| 6,007,529 | A * | 12/1999 | Gustafsson | A61J 1/00 604/410 |
| 6,694,157 | B1 * | 2/2004 | Stone | A61B 5/14539 356/39 |
| 2003/0065149 | A1 * | 4/2003 | McGinnis | A61J 1/10 530/385 |
| 2012/0301908 | A1 * | 11/2012 | Jungerius | G01N 33/96 435/14 |

OTHER PUBLICATIONS

Maas et al., "30. New hemoglobin-based reference material suitable for all type of Hemoximeters," Ned Tijdschr Klin Chem, vol. 22, No. 3, Jan. 1, 1997, p. 125.

* cited by examiner

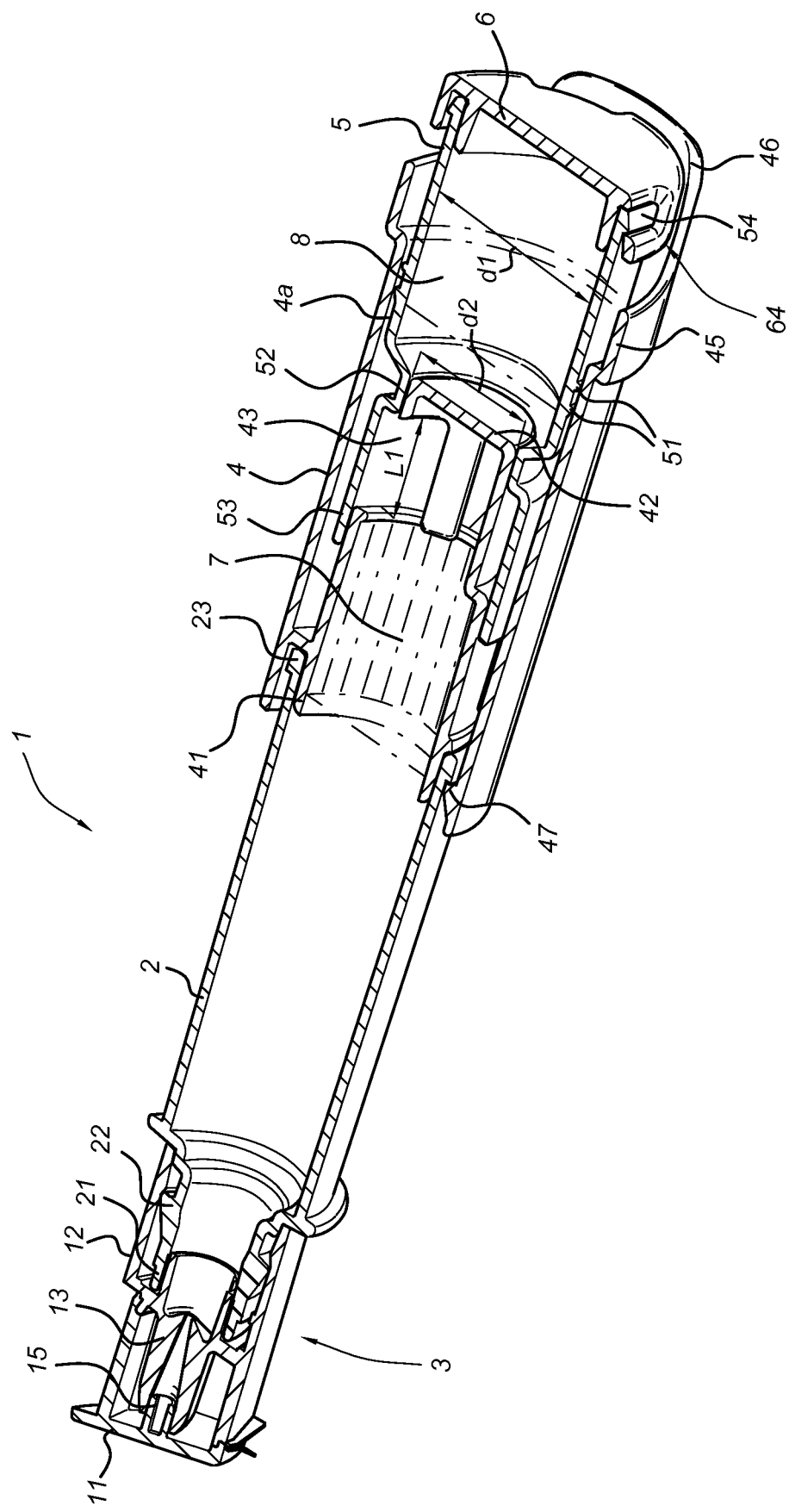

CONTAINER COMPRISING HAEMOGLOBIN FRACTIONS

CROSS REFERENCE TO RELATED APPLICATIONS

This application is a 35 USC § 371 national stage application of PCT/EP2015/079294, which was filed Dec. 10, 2015 and claims priority to European Patent Application No. 14199807.0, filed Dec. 22, 2014, both of which are incorporated herein by reference as if fully set forth.

FIELD OF THE INVENTION

The present invention relates to a container comprising hemoglobin fractions, wherein said container comprises at least two compartments, wherein a first compartment comprises O2Hb (oxyhaemoglobin) and a second compartment comprises MetHb (methaemoglobin), optionally wherein O2Hb is stabilized. The invention also relates to a kit for determining the reliability of a CO-oximetry device, wherein said kit comprises said container and to a method for determining the reliability of a CO-oximetry device using said container.

BACKGROUND OF THE INVENTION

Blood is a complex medium containing both cellular and non-cellular components. The principal protein of the cellular components is haemoglobin which transports oxygen. The analysis of patient's blood to determine the total amount of haemoglobin (tHb) and the different haemoglobin fractions is useful to a physician in evaluating the respiratory status of the patient. Examples of haemoglobin fractions are oxygenated haemoglobin (oxyhaemoglobin, O2Hb), oxidized haemoglobin (methaemoglobin or haemiglobin, MetHb), haemoglobin complexed with carbon monoxide (carboxyhaemoglobin, COHb), reduced haemoglobin (deoxyhaemoglobin, HHb), haemoglobin complexed with sulfur (sulfhemoglobin, SHb) and haemoglobin complexed with cyanide (cyanmethaemoglobin, CNMetHb). In general, O2Hb oxidizes over time, becoming MetHb. MetHb cannot bind oxygen, which is detrimental to the subject in which the MetHb has formed. For this, most organisms feature enzymes such as MetHb reductase, which convert MetHb back to O2Hb.

"CO-oximetry," sometimes referred to as cooxymetry, generally refers to the process, often automated, in which a plurality of wavelengths is used to quantitate several haemoglobin fractions, in the same sample. The number of wavelengths required is equal to or greater than the number of haemoglobin fractions in the sample. The specific wavelengths employed depend, at least in part, on the haemoglobin fractions to be determined, the spectral response curves thereof and the quality of the filters or diffraction gratings used to isolate light having the selected specific wavelengths.

In order to ensure accurate results, a CO-oximeter requires a clearly defined quality control program. Such a program typically includes the analysis of samples having known concentrations of the various haemoglobin fractions. For these samples, in which the simultaneous presence of MetHb and O2Hb is required at known and reliable concentration levels, it is a problem that O2Hb can oxidize to MetHb. This oxidation renders neither the O2Hb concentration nor the MetHb concentration reliable or constant. In such samples, the use of MetHb reductase to regenerate O2Hb that has oxidized is not a solution to this problem, because it substantially depletes the desired concentration of MetHb as well. Access to good and reliable CO-oximetry control samples, which preferably feature both MetHb and O2Hb, is desirable.

Most CO-oximetry controls are based on dyes (see for example EP 132 399). Such controls are not attractive as their spectrophotometric characteristics are not the same as those of haemoglobin fractions in blood samples.

Other CO-oximetry controls are hemolysate based controls (see for example U.S. Pat. No. 4,485,174, US 2003/0068822 or US 2012/0104323). Using these controls it is not possible to have different constant and known levels of O2Hb and MetHb in the same sample.

A lyophilized bovine haemoglobin preparation containing a mixture of various fractions of O2Hb, COHb and MetHb had also been used as CO-oximetry controls. This preparation is assumed to be spectrophotometrically equivalent with a fresh bovine haemoglobin solution (Maas et al, Clinical Chemistry, 44:11, 2331-2339 (1998). However, this preparation needs to be reconstituted before use and lyophilization process and/or additives used for lyophilization may cause matrix effects.

Therefore there is still a need for improved CO-oximetry controls that do not have the drawbacks of the ones of the prior art. The CO-oximetry controls of the invention are liquid, ready-to-use, have different, custom, and reliable levels of O2Hb, COHb and MetHb and no or minimal matrix effect is expected when using the controls on different CO-oximetry analyzers.

BRIEF DESCRIPTION OF THE DRAWINGS

FIG. 1 shows a cross sectional view of an embodiment of the storage assembly according to the present invention.

DESCRIPTION OF THE INVENTION

The inventors found that by storing the different haemoglobin fractions separately and mixing them before use, in other words that by storing the incompatible haemoglobin fractions separately and mixing them before use, it is possible to obtain a liquid ready-to-use CO-oximetry control with different levels of O2Hb, COHb and MetHb without or with minimal matrix effects.

Container

In a first aspect there is provided a container comprising haemoglobin fractions, wherein said container comprises at least two compartments, wherein a first compartment comprises O2Hb (oxyhaemoglobin) and a second compartment comprises MetHb (methaemoglobin), optionally wherein O2Hb is stabilized.

A container may be any recipient suitable to be used in a laboratory as long as it is arranged to comprise the two compartments holding the haemoglobin fractions separately. The invention provides that said compartments should be adjacent to each other. As such, there is provided a container comprising haemoglobin fractions, wherein said container comprises at least two adjacent compartments, wherein a first compartment comprises O2Hb (oxyhaemoglobin) and a second compartment comprises MetHb (methaemoglobin), optionally wherein O2Hb is stabilized.

Alternatively, the present invention embodiments may be implemented using a storage assembly as described in International patent publication WO2014/142655, wherein the haemoglobin fractions are stored in the separate first and second storage chambers. The expression "haemoglobin fraction" may be replaced by "haemoglobin species" or "haemoglobin form" or "haemoglobine portion" or "haemoglobin derivative".

A haemoglobin fraction may be derived from the haemoglobin present in blood using any technique known to the skilled person. Within the context of the invention, the word "haemoglobin" refers to the total amount of haemoglobin (tHb), i.e. all existing haemoglobin fractions.

"A haemoglobin fraction" may refer to or may comprise or may consist of or may be derived from at least one of the following haemoglobin fraction: the fraction oxygenated haemoglobin (oxyhaemoglobin, O2Hb), the fraction oxidized haemoglobin (methaemoglobin or haemiglobin, MetHb), the fraction haemoglobin complexed with carbon monoxide (carboxyhaemoglobin, COHb), the fraction reduced haemoglobin, (HHb), the fraction haemoglobin complexed with sulfur (sulfhemoglobin, SHb) and the fraction haemoglobin complexed with cyanide (cyanomethemoglobin, CNMetHb). O2Hb is the haemoglobin fraction wherein O2 is bound to the haemoglobin molecule. Depending on the conditions, O2 could be liberated to form HHb. This reaction is reversible. MetHb is a haemoglobin fraction wherein O2 could not bind due to oxidation of the iron molecule. Reduction of the iron in MetHb leads to HHb or O2Hb. COHb is a haemoglobin fraction wherein CO is bound instead of O2. Although the affinity of hemoglobin for CO is 200 to 250 times as great as the affinity of haemoglobin for oxygen, COHb can be converted into O2Hb or HHb.

Throughout the application, the word "O2Hb" may be replaced by the expression "a or the haemoglobin fraction O2Hb" depending on the context. The same holds for other haemoglobin fractions.

Within the context of the invention, a O2Hb haemoglobin fraction may mean that at least 75%, 80%, 85%, 90%, 95%, 96%, 97%, 98%, 99% or 100% of the haemoglobin present in a preparation is bound to O2.

Within the context of the invention, a COHb haemoglobin fraction may mean that at least 75%, 80%, 85%, 90%, 95%, 96%, 97%, 98%, 99% or 100% of the haemoglobin present in a preparation is bound to CO.

Within the context of the invention, a MetHb haemoglobin fraction may mean that the iron molecule of at least 75%, 80%, 85%, 90%, 95%, 96%, 97%, 98%, 99% or 100% of the haemoglobin present has been oxidized.

In a preferred embodiment, a haemoglobin fraction does not comprise any cells, more preferably does not comprise any blood cells, even more preferably does not comprise any white and red blood cells. In a more preferred embodiment, a haemoglobin fraction is a cell-free fraction. However, it is not excluded by the invention that some cells may be present in a haemoglobin fraction. However, preferably the O2Hb haemoglobin fraction does not comprise any cells. Under physiological conditions the volume percentage of red blood cells in blood may be from 20 to 60%. Therefore the volume percentage of cells in a haemoglobin fraction (O2Hb and/or MetHb) may be from 0 to 70%.

The fractions referred to herein are preferably cell-free fractions. As a result of this the containers of various embodiments of the present invention do not derive their ability to stably store fractions from the physical separation between cells and other substances. In a preferred embodiment, a container of the invention comprises O2Hb and MetHb as haemoglobin fractions, each of them being present in one compartment of the container.

O2Hb Fraction

An O2Hb fraction may be derived from the haemoglobin present in blood using any technique known to the skilled person. Preferably, blood is treated with an anticoagulant and centrifuged to remove the plasma and the buffycoat (i.e. white blood cells and platelets). Preferably, heparin is used as an anti-coagulant. Preferably the centrifugation is during 15 minutes, at 3000 g. Any other method known to the skilled person to centrifuge the blood may be used.

The cells obtained after the centrifugation and removal of the plasma and the buffycoat comprises the red blood cells comprising the haemoglobin. The cells may be washed. Preferably the cells are washed twice. More preferably, the cells are washed with 0.9% NaCl. After washing, a buffer may be added to these cells to dilute the haemoglobin to a desired concentration. Preferably the haemoglobin concentration is 5-30 g/dL after dilution. In a more preferred embodiment the haemoglobin concentration is 10-25 g/dL after dilution, or 20-30 g/dL after dilution. In a most preferred embodiment, the haemoglobin concentration is 25-26 g/dL after dilution.

A preferred diluting buffer is one of the buffers described by Norman E. Good, also known as Good buffers (Norman E. Good et al, Hydrogen Ion buffers for biological research, Biochemistry, 1966, 5(2), pp 467-477). A more preferred buffer is 0.1-0.2 M TAPSO (3-[N-(tris-hydroxymethyl) methyl amino]-2-hydroxypropane sulfonic acid) pH 8.0.

O2Hb is preferably obtained from the previous blood cells as follows: 25% (v/v) toluene is preferably added to the diluted cells, the mixture may be stirred for 10-120 minutes. Preferably the mixture is stirred for 30-100 minutes, more preferably the mixture is stirred for 60 minutes. After stirring the mixture is placed in a separating funnel at 2-8° C. for 12-24 hours. Preferably the mixture is placed at 2-8° C. for 18 hours.

The hemolysate is preferably separated and centrifuged for 30 minutes at 2700 g, filtered and centrifuged for 90 minutes at 13000 g to remove the remaining cell debris and stromae.

The supernatant obtained comprises the O2Hb fraction. This supernatant may be diluted in a suitable buffer. Preferably one of the Good buffers is used. More preferably, the buffer has a pKa of 7.0-8.0, even more preferably the buffer is TAPSO, even more preferably at a final concentration of 0.1 M, pH 7.4.

The supernatant (i.e called hemolysate) is subsequently centrifuged (preferably 30 minutes at 2700 g) to remove any precipitate. The second supernatant obtained comprises the O2Hb fraction in an even more purified form.

In a preferred embodiment, the O2Hb fraction is stabilized. Any way of stabilizing the O2Hb fraction known to the skilled person could be used in the present invention. A skilled person appreciates that a stabilized O2Hb fraction relates to a fraction where the fraction of O2Hb within the total Hb fraction is constant at a dynamic equilibrium in a steady state, and that stabilization thus does not entail fixation of an oxygenated state of individual Hb compounds.

Examples of stabilisation of O2Hb are addition of protein stabilizers or addition of metal chelating agents such as Ethylenediaminetetraacetic acid (EDTA).

An O2Hb fraction is defined as having been stabilized when the percentage of haemoglobin which is bound to O2 does not change more than 1%, 2%, 3%, 4%, 5%, 6%, 7%, 8%, 9%, 10%.

In a preferred embodiment, the O2Hb fraction is stabilized using a MetHb reductase. MetHb reductase may be isolated from cell membrane. A commercially available MetHb reductase may also be used. MetHb reductase can convert MetHb to O2Hb.

In a more preferred embodiment, NAD and Na-lactate are added to the O2Hb fraction together with a MetHb reductase. In the MetHb reductase system NADH (the reduced form of nicotinamide adenine dinucleotide) acts as an electron donor to the ferric ion in methaemoglobin. By adding NAD (the oxidized form of nicotinamide adenine dinucleotide) and lactate to the system, a source of NADH cofactor is provided. NAD acts as a proton acceptor which leads to the formation of NADH.

NAD is preferably added in a concentration of 0.5-1.0 mM, more preferably in a concentration of 0.7 mM. Na-lactate is preferably added in a concentration of 0.02-0.1 M, more preferably in a concentration of 0.06 M.

The O2Hb solution may be sterilized. The sterilization is preferably carried out using 0.2 µm filters.

It is clear for the skilled person that a container of the invention could be prepared comprising any concentration or any amount of O2Hb in a compartment of said container. Alternatively, O2Hb present is expressed as the percentage of the total amount of haemoglobin present in the container of the invention. Examples of such possible percentage are: 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%.

1% O2Hb means that 1% of the total haemoglobin amount present in the container of the invention is O2Hb. If only two fractions of haemoglobins are present in the container of the invention, it therefore means that 99% of the total haemoglobin amount is represented by MetHb. The same holds for any other percentage as indicated above.

MetHb Fraction

A MetHb fraction may be derived from the haemoglobin present in blood using any technique known to the skilled person. Preferably, blood is treated with an anticoagulant and centrifuged to remove the plasma and the buffycoat (i.e. white blood cells and platelets). Preferably, heparin is used as an anti-coagulant. Preferably the centrifugation is during 15 minutes, at 3000 g. Any other method known to a skilled person to centrifuge the blood and remove the plasma may be used.

Subsequently, leucocytes are removed by a leucocyte filter and the red blood cells are lysed by adding two volumes of cold water. Such filtration is preferably carried out as described in the examples.

Stroma is subsequently removed by tangential flow filtration and the hemolysate is subsequently concentrated to the desired haemoglobin concentration using tangential flow filtration. In a preferred embodiment, said tangential flow filtration and subsequent concentration are carried out as described in the examples.

The haemoglobin obtained is preferably converted to MetHb by adding 0.5-1.5 mmol $NaNO_2$ per mmol oxyhaemoglobin, more preferably by adding 0.65-0.85 mmol $NaNO_2$ per mmol oxyhaemoglobin.

Any other method known to a skilled person to convert the haemoglobin to MetHb may be used, examples are adding azide or letting O2Hb be naturally converted into MetHb.

The MetHb solution may be sterilized and filled in one compartment of the container. The sterilization is preferably carried out using 0.2 µm filters.

It is clear for the skilled person that a container of the invention could be prepared comprising any concentration or any amount of MetHb in a compartment of said container. Alternatively, MetHb present is expressed as the percentage of the total amount of haemoglobin present in the container of the invention. Examples of such possible percentage are: 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%.

1% MetHb means that 1% of the total haemoglobin amount present in the container of the invention is MetHb. If only two fractions of haemoglobins are present in the container of the invention, it therefore means that 99% of the total haemoglobin amount is represented by O2Hb. The same holds for any other percentage as indicated above.

A preferred container of the invention is a container comprising at least two compartments, wherein a first compartment comprises 10% O2Hb (oxyhaemoglobin) and a second compartment comprises 90% MetHb (methaemoglobin), optionally wherein O2Hb is stabilized.

Another preferred container of the invention is a container comprising at least two compartments, wherein a first compartment comprises 20% O2Hb (oxyhaemoglobin) and a second compartment comprises 80% MetHb (methaemoglobin), optionally wherein O2Hb is stabilized.

Another preferred container of the invention is a container comprising at least two compartments, wherein a first compartment comprises 30% O2Hb (oxyhaemoglobin) and a second compartment comprises 70% MetHb (methaemoglobin), optionally wherein O2Hb is stabilized.

Another preferred container of the invention is a container comprising at least two compartments, wherein a first compartment comprises 40% O2Hb (oxyhaemoglobin) and a second compartment comprises 60% MetHb (methaemoglobin), optionally wherein O2Hb is stabilized.

Another preferred container of the invention is a container comprising at least two compartments, wherein a first compartment comprises 50% O2Hb (oxyhaemoglobin) and a second compartment comprises 50% MetHb (methaemoglobin), optionally wherein O2Hb is stabilized.

Another preferred container of the invention is a container comprising at least two compartments, wherein a first compartment comprises 60% O2Hb (oxyhaemoglobin) and a second compartment comprises 40% MetHb (methaemoglobin), optionally wherein O2Hb is stabilized.

Another preferred container of the invention is a container comprising at least two compartments, wherein a first compartment comprises 70% O2Hb (oxyhaemoglobin) and a second compartment comprises 30% MetHb (methaemoglobin), optionally wherein O2Hb is stabilized.

Another preferred container of the invention wherein said container comprises at least two compartments, wherein a first compartment comprises 80% O2Hb (oxyhaemoglobin) and a second compartment comprises 20% MetHb (methaemoglobin), optionally wherein O2Hb is stabilized.

Another preferred container of the invention is a container comprising at least two compartments, wherein a first compartment comprises 90% O2Hb (oxyhaemoglobin) and a second compartment comprises 10% MetHb (methaemoglobin), optionally wherein O2Hb is stabilized.

In a further preferred embodiment of the invention, the container comprises another haemoglobin fraction. This "another" or "additional" haemoglobin fraction may comprise COHb (carboxyhemoglobin) and/or other fractions as SHb or CNMetHb and may be present in the first and/or second compartment of the container of the invention. A COHb fraction and/or other fractions as SHb or CNMetHb may be present in the first or in the second compartment of the container. It means that the COHb fraction and/or other fractions as SHb or CNMetHb may be together with the O2Hb fraction. It is also possible that the COHb fraction and/or other fractions as SHb or CNMetHb is together with the MetHb fraction. The same holds for HHb.

A COHb fraction could be prepared using any technique known to the skilled person. Preferably, a COHb fraction is obtained by converting a O2Hb fraction into a COHb fraction by adding carbon monoxide.

It is clear for the skilled person that a container of the invention could be prepared comprising any concentration or amount of COHb in a compartment of said container. Alternatively, COHb present is expressed as the percentage of the total amount of haemoglobin present in the container of the invention. Examples of such possible percentage are: 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%.

A HHb fraction could be prepared using any technique known to the skilled person. An example of such a technique is adding ammoniated Stokes' reagent (FeSO4 and tartaric acid) to O2Hb.

It is clear for the skilled person that a container of the invention could be prepared comprising any concentration or amount of HHb in a compartment of said container. Alternatively, HHb present is expressed as the percentage of the total amount of haemoglobin present in the container of the invention. Examples of such possible percentage are: 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%.

Another preferred container of the invention is a container comprising at least two compartments, wherein a first compartment comprises 90% O2Hb (oxyhaemoglobin) and a second compartment comprises 5% MetHb (methaemoglobin), optionally wherein O2Hb is stabilized. In this preferred embodiment, 5% COHb is present either in the first or in the second compartment of the container.

Another preferred container of the invention is a container comprising at least two compartments, wherein a first compartment comprises 80% O2Hb (oxyhaemoglobin) and a second compartment comprises 10% MetHb (methaemoglobin), optionally wherein O2Hb is stabilized. In this preferred embodiment, 10% COHb is present either in the first or in the second compartment of the container.

Another preferred container of the invention is a container comprising at least two compartments, wherein a first compartment comprises 70% O2Hb (oxyhaemoglobin) and a second compartment comprises 15% MetHb (methaemoglobin), optionally wherein O2Hb is stabilized. In this preferred embodiment, 15% COHb is present either in the first or in the second compartment of the container.

Another preferred container of the invention is a container comprising at least two compartments, wherein a first compartment comprises 60% O2Hb (oxyhaemoglobin) and a second compartment comprises 20% MetHb (methaemoglobin), optionally wherein O2Hb is stabilized. In this preferred embodiment, 20% COHb is present either in the first or in the second compartment of the container.

Another preferred container of the invention is a container comprising at least two compartments, wherein a first compartment comprises 50% O2Hb (oxyhaemoglobin) and a second compartment comprises 25% MetHb (methaemoglobin), optionally wherein O2Hb is stabilized. In this preferred embodiment, 25% COHb is present either in the first or in the second compartment of the container.

Another preferred container of the invention is a container comprising at least two compartments, wherein a first compartment comprises 40% O2Hb (oxyhaemoglobin) and a second compartment comprises 30% MetHb (methaemoglobin), optionally wherein O2Hb is stabilized. In this preferred embodiment, 30% COHb is present either in the first or in the second compartment of the container.

Each of the haemoglobin fractions referred to herein is derived from blood. Preferably, the blood is from a mammalian animal. More preferably, the mammalian blood is bovine blood or human blood. As known to a person skilled in the art, the source of haemoglobin fractions can have an impact on the composition of said haemoglobin fraction. This is for instance the case with the presence of trace substances in the fractions. For example, substances that are present in human blood but not in bovine blood can be present in a haemoglobin fraction derived from human blood, perhaps as a trace substance, but not in a haemoglobin fraction derived from bovine blood, not even as a trace substance. It follows that the source of the blood from which the haemoglobin fractions are derived thus can have an effect on the haemoglobin fractions themselves. Because the haemoglobin fractions are comprised within the container of the invention, the source of the haemoglobin fractions thus also affects the contents of the container of the invention. The container of the invention is not an empty container.

It is clear for the skilled person that the concentration of total haemoglobin is not limited to one concentration. Examples of possible concentrations include: 8, 9, 10, 11, 12, 13, 14, 15, 16, 17, 18, 19, 20, 21, 22, 23, 24, 25 or 26 g/dL.

It is also clear for the skilled person that the container of the invention may also comprise an analyte. Such an analyte is preferably an analyte that is relevant in clinical chemistry, and that is not O2Hb, MetHB, or COHb. The presence and preferably quantity of such analyte may for example be assessed via spectrophotometry. For example a container may comprise bilirubine and/or glucose, or other analytes that are relevant in clinical chemistry. Preferred analytes are analytes that can be assessed via spectrophotometry. In this context, assessment of an analyte can mean the detection of the presence of an analyte, or the determination of the concentration with which such an analyte is present. Such analyte may be present in a compartment with O2Hb and/or in a compartment with MetHb. Alternatively, one analyte may be present with O2Hb and another analyte may be present with MetHb. A preferred embodiment is therefore a container as described earlier herein, wherein an additional analyte is present in a compartment of said container. A more preferred embodiment is a container as described above, wherein said additional analyte is an analyte that can be assessed via spectrophotometry. An even more preferred embodiment is a container as described above, wherein said additional analyte is bilirubine or glucose, most preferably bilirubine.

The present invention in a further embodiment provides a container comprising haemoglobin fractions, wherein said container comprises at least two compartments, wherein a first compartment comprises O2Hb (oxyhaemoglobin) and a second compartment comprises MetHb (methaemoglobin), optionally wherein O2Hb is stabilized, wherein the at least two compartments are part of an assembly arranged for separately storing the haemoglobin fractions. In a preferred embodiment, said compartments are adjacent compartments.

A more preferred embodiment is a container wherein the at least two compartments are part of an assembly arranged for separately storing the haemoglobin fractions, the assembly further comprising a mixing arrangement providing a communication channel between the at least two compartments for mixing the haemoglobin fractions directly prior to use. A further more preferred embodiment is a container comprising haemoglobin fractions, wherein said container comprises at least two compartments that can be adjacent to each other, wherein a first compartment comprises O2Hb (oxyhaemoglobin) and a second compartment comprises MetHb (methaemoglobin), optionally wherein O2Hb is stabilized, wherein the at least two compartments are part of an assembly arranged for separately storing the haemoglobin fractions, the assembly further comprising a mixing arrangement providing a communication channel between the at least two compartments for mixing the haemoglobin fractions directly prior to use. The present invention in a further embodiment provides a container wherein the at least two compartments feature a communication channel between each other. As such, the invention provides a container comprising haemoglobin fractions, wherein said container comprises at least two compartments, further comprising a communication channel between the at least two compartments, wherein a first compartment comprises O2Hb (oxyhaemoglobin) and a second compartment comprises MetHb (methaemoglobin), optionally wherein O2Hb is stabilized. In a preferred embodiment, said at least two compartments are adjacent compartments.

The configuration of at least two compartments and mixing arrangement may be such that it allows introducing a dose of O2Hb from one compartment, into a second compartment holding MetHb, or introducing a dose of MetHb from one compartment, into a second compartment holding O2Hb.

Such an assembly may be an embodiment as described in international patent publication WO2007/040396, which is incorporated herein by reference. The assembly comprises a dosing part and a supply part, which dosing part is arranged for receiving a dose of the mixing substance (e.g. holding one of the haemoglobin fractions O2Hb or MetHb) and which supply part comprises an outlet for introducing the dose into the container (already holding the other one of the haemoglobin fractions: MetHb or O2Hb respectively). The dosing part and the supply part may be configured to cooperate with one another, such that a pressure chamber having a changeable volume is formed adjacent to the outlet when the supply part and the dosing part are joined together, which pressure chamber functions to enable a pumping action for pumping the dose into and out of the container (and thus mixing the haemoglobin fractions O2Hb and MetHb). In a further embodiment, the aforementioned dosing part and supply part are adjacent to each other.

In preferred embodiments, the container comprising at least two compartments forms a unity. In such preferred embodiments, the container comprising at least two compartments forms an assembly. As such, whenever this document refers to a container, it could be read as a container assembly. A preferred container assembly is a container assembly that essentially consists of at least two compartments, wherein a first compartment comprises O2Hb (oxyhaemoglobin) and a second compartment comprises MetHb (methaemoglobin), optionally wherein O2Hb is stabilized, optionally wherein said compartments are adjacent compartments. In a more preferred embodiment, a container of the invention essentially consists of the at least two compartments, arranged for separately storing the haemoglobin fractions, the assembly further comprising a mixing arrangement providing a communication channel between the at least two compartments for mixing the haemoglobin fractions directly prior to use.

A further preferred embodiment of the invention is a container assembly comprising haemoglobin fractions, wherein said container assembly comprises at least two assembled compartments, wherein a first compartment comprises O2Hb (oxyhaemoglobin) and a second compartment comprises MetHb (methaemoglobin), optionally wherein O2Hb is stabilized. A more preferred embodiment is a container assembly comprising haemoglobin fractions, wherein said container assembly comprises at least two assembled compartments that can be brought in fluid communication with each other, wherein a first compartment comprises O2Hb (oxyhaemoglobin) and a second compartment comprises MetHb (methaemoglobin), optionally wherein O2Hb is stabilized. An even more preferred embodiment is a container assembly comprising haemoglobin fractions, wherein said container assembly comprises at least two assembled compartments that can be brought in fluid communication with each other, wherein a first compartment comprises O2Hb (oxyhaemoglobin) and a second compartment comprises MetHb (methaemoglobin), optionally wherein O2Hb is stabilized.

Alternatively, the container according to the present invention may be embodied as a storage assembly according to one of the embodiments described in international patent publication WO2014/142655, which is incorporated herein by reference. Such a storage assembly for two substances to be mixed (i.e. O2Hb and MetHb) prior to use is shown schematically in FIG. 1 and in the embodiment shown comprises a closable dropper tip 3. A first storage chamber 7 (holding one of the haemoglobin fractions, O2Hb or MetHb) is formed by the closable dropper tip 3 and a first container part 2, 4, the first container part 2, 4 being provided with at least one aperture 43. A second storage chamber 8 (holding the other haemoglobin fraction, MetHb or O2Hb respectively) is formed by a second container part 5 which comprises an open end part 52, 53 that closes off the at least one aperture 43 in a first operational position. The first and second container part 2, 4; 5, 6 are moveable with respect to each other, and are in fluid communication through the at least one aperture 43 in a second operational position wherein the total flow surface area of the at least one aperture 43 is at least equal to a cross sectional area of the first container part 2, 4.

FIG. 1 shows a cross sectional view of an embodiment of the storage assembly according to the present invention.

FIG. 1 shows a cross sectional view of an embodiment of a storage assembly 1 according to the present invention, comprising a closable dropper tip 3 and a first storage chamber 7 formed by a first container part 2, 4 and the closable dropper tip 3. The closable dropper tip 3 is fluid-tightly connected to a canister 2 of the first container part 2, 4, using e.g. a rim 22 near a first end 21 of the canister 2 engaging an inner surface of a dropper tip body 12.

In the embodiment shown, the first container part 2, 4 further comprises a tubular part 4, fluid tightly coupled to a second end 23 of the canister 2, using a first end 41 of the tubular part 4 of which the outer diameter matches the inner diameter of the second end 23 of the canister 2. The coupling can be further enhanced using e.g. snap fit parts 47 shown in FIG. 1, which are dimensioned to engage a rim provided at the second end 23. The tubular part 4 is provided with at least one aperture 43 extending over a part of the circumference of the tubular part 4 near an internal end surface 42 thereof. These apertures 43 are closed off in the first operational position of the assembly as shown in FIG. 1 by an open end part 53 being part of a second container part 5. E.g. as shown in the embodiment of FIG. 1, the inner diameter of the open end part 53 is matched to provide a fluid tight coupling to an outside diameter of the end of the tubular part 4. Thus the first storage chamber 7 is formed by the inner surfaces of the canister 2, closable dropper tip 3, tubular part 4, and the open end part 53.

A second storage chamber 8 is adjacent to first storage chamber 7, forming two adjacent compartments; storage chamber 8 is formed by the inner surfaces of the second container part 5 and the outer surface of the second end 42 of the tubular part 4. In the embodiment shown the second container part 5 comprises an optional closing cap 6. The second container part 5 may be provided with one or more snap fit element 54 latching behind corresponding latch apertures 64 of the closing cap 6. In an alternative embodiment, the second container part 5 is provided as a single piece.

The first container part 2, 4 and second container part 5 are moveable with respect to each other. In the specific embodiment shown, this is made possible by the tubular part 4 comprising an inner surface 4a matching an outer surface of the second container part 5.

When moving to the second operational position of the storage assembly, the first chamber 7 and second chamber 8 are brought in fluid communication with each other through the at least one aperture 43 which acts as a communications channel, thus providing a very easy and convenient way to activate the product by allowing the two substances to mix. The at least one aperture 43 thus provides a mixing arrangement and will be opened over almost the entire length L1 thereof (see FIG. 1), as a result of which the total flow surface area of the at least one aperture 43 is at least equal to a cross sectional area of the first container part 2, 4. As a result, after activation of the storage assembly 1, no flow resistance occurs which allows a very gentle mixing, without violent motion of the substances to be mixed. Especially when needing to mix certain types of substances where only a low shear is permitted, such as in the case of substances comprising protein, albumin, whole blood cells or substances comprising a surfactant, only very gentle mixing is allowed. It follows that a preferred embodiment of the invention is a container comprising haemoglobin fractions, wherein said container comprises at least two compartments that can be brought in fluid communication with each other, wherein a first compartment comprises O2Hb (oxyhaemoglobin) and a second compartment comprises MetHb (methaemoglobin), optionally wherein O2Hb is stabilized. A more preferred embodiment is a container comprising haemoglobin fractions, wherein said container comprises at least two adjacent compartments that can be brought in fluid communication with each other, wherein a first compartment comprises O2Hb (oxyhaemoglobin) and a second compartment comprises MetHb (methaemoglobin), optionally wherein O2Hb is stabilized. In preferred embodiments, fluid communication is achieved through the intended operation of the container alone, for example as described above, without the need for external utilities such as pipettes or sampling robots. As such, in this application, whenever at least two compartments are said to be able to be brought in fluid communication with each other, it is to be construed that said at least two compartments are part of an assembly that is arranged for bringing said at least two compartments in fluid communication with each other.

In a further embodiment, the first storage chamber 7 comprises O2Hb and the second storage chamber 8 comprises MetHb.

Alternatively, in another embodiment, the second storage chamber 8 comprises O2Hb and the first storage chamber 7 comprises MetHb.

The following are further embodiments or considerations relating to the container of the invention:

Objects that comprise multiple components yet still form a unity, such as the container assembly or the container as described above, are well known. Examples are a bicycle or a corked bottle of wine. Because preferred embodiments of the invention form a unity, it follows that in preferred embodiments of the invention, the container is not a refrigerator that contains further containers that each contain haemoglobin fractions. Similarly, in preferred embodiments, the container is not a box or any other storage means that contains or displays individual containers comprising haemoglobin fractions. In preferred embodiments, the compartments of the container or of the container assembly are in a contacting engagement that provides a mechanical link. A non-limiting examples of such a contacting engagement that provides a mechanical link is a nail in a board. In preferred embodiments of the invention, the container does not disassemble into its separate compartments merely when it is positioned under a certain angle, or in a certain way. In preferred embodiments, the container or the compartments are not made of one solid or continuous piece of material. In preferred embodiments, the compartments that are comprised in the container are not organized as in an array, or as on a grid. Containers of the invention allow for the provision of reliable standards for CO-Oximetry, that is to say for the provision of reliable CO-oximetry controls, which feature known and stable concentrations of Hb fractions. The controls do not have the drawbacks of the ones of the prior art. The CO-oximetry controls provided by the containers of the invention are liquid, ready-to-use, have different levels of actual O2Hb, COHb and MetHb, do not feature artificial dyes, and no or minimal matrix effect is expected when using the controls on different CO-oximetry analyzers.

Kit

In a further aspect, there is provided a kit for determining the reliability of a CO-oximetry device, the kit comprises (i) at least one container as defined in the first aspect, and (ii) instructions for mixing the haemoglobin fractions contained within the container to obtain one or more control samples, and for measuring the concentration of a haemoglobin fraction present using said device. This kit comprises the CO-oximetry controls of the invention.

Preferably, the kit is ready to use once the haemoglobin fractions have been mixed together. The container of the invention comprising CO-oximetry controls is quite attractive compared to existing CO-oximetry controls since the container is ready to use and could be stored for more than 1, 2, 3, 4 weeks or 1, 2, 3, 4, 5, 6, 7, 8, 9, 10, 11, 12, months or longer without a change in any substantial amount of any of the haemoglobin fractions. Once the haemoglobin fractions have been mixed together, the CO-oximetry controls could be used within 1, 5, 10, 15, 20, 30, 35, 40, 45, 50, 55, 60 minutes or 1, 2, 3, 4, 5, 6, 7, 8 hour or longer without a change in any substantial amount of the haemoglobin fractions. "Without a change in any substantial amount" preferably means a change of less than 10%, 9%, 8%, 7%, 6%, 5%, 4%, 3%, 2%, 1% or less than the initial or original amount of the haemoglobin fractions. A change may be a decrease or an increase of the amount of a haemoglobin fraction.

Method

In a further aspect, there is provided a method for determining the reliability of a CO-oximetry device, comprising the following successive steps:
a) mixing haemoglobin fractions present in a container as defined herein to obtain one control sample having defined concentrations of haemoglobin fractions;
b) measuring, by means of the device, the concentration of a haemoglobin fraction present in the control sample of step a);
c) determining the reliability of the device on the basis of the difference between (i) the known concentrations of the haemoglobin fractions of the sample obtained at the end of step a) and (ii) the result of the measurement of the measurement of step b).

General

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a container, a kit or a method as defined herein may comprise additional component(s), respectively part(s), respectively step(s) than the ones specifically identified, said additional component(s), respectively part(s), respectively step(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

Each of the numerical values "x" disclosed in the description especially in the context of a temperature, time, speed, concentration in a method for preparing a haemoglobin fraction is not limited to the exact value "x" disclosed. The application encompasses the value "x" more or less 1% of said value.

In this document, when compartments are described as being adjacent, it is also to be construed that said compartments are adjoining. A skilled person will know what adjacent/adjoining compartments are. Adjacent/adjoining compartments are most often mechanically connected to one another. Non-limiting examples of mechanical connections are that the adjacent compartments share a partitioning wall and cannot be separated, or that the adjacent compartments are in a contacting engagement with each other, or that the adjacent compartments are in a contacting engagement with an engaging structure that thus is in contacting engagement with both adjacent compartments, mechanically connecting the adjacent compartments. Adjacent compartments can share a partitioning surface, or they can be independent but very close to each other, preferably not more than 100, 90, 80, 70, 60, 50, 40, 30, 20, 10, 9, 8, 7, 6, 5, 4, 3, 2, or 1 mm apart. Preferably, there is no other element in between adjacent elements. All patent and literature references cited in the present specification are hereby incorporated by reference in their entirety. The following examples are offered for illustrative purposes only, and are not intended to limit the scope of the present invention in any way.

EXAMPLES

All chemicals were obtained from Sigma-Aldrich.

Example 1: Preparation of Oxyhaemoglobin

Blood was drawn from cows using heparin as an anticoagulant and centrifuged (15 minutes, 3000 g) to remove the plasma and the buffycoat.

The red cells were washed twice with 0.9% NaCl and 0.1 M TAPSO (3-[N-(tris-hydroxymethyl)methyl amino]-2-hydroxypropane sulfonic acid) pH 8.0 was added to dilute to the desired haemoglobin concentration.

25% (v/v) toluene was added, the mixture was stirred for one hour at room temperature and placed in a separating funnel at 2-8° C. for 18 hours.

The hemolysate was separated and centrifuged for 30 minutes at 2700 g, filtered over a paper filter and centrifuged for 90 minutes at 13000 g.

TAPSO was added to a final concentration of 0.1 M pH 7.4.

0.7 mM NAD (the oxidized form of nicotinamide adenine dinucleotide) and 0.06 M Na-lactate was added to provide a source of NADH cofactor to the MetHb reductase system.

The hemolysate was centrifuged (30 minutes at 2700 g) to remove any precipitate.

The hemolysate was sterilized using 0.2 µm filters (AcroPak 200, obtained from VWR International B.V., Netherlands).

The resulting hemolysate consists of 90-100% oxyhaemoglobin.

Example 2: Preparation of Methaemoglobin

Blood was drawn from cows using heparin as an anticoagulant and centrifuged (15 minutes, 3000 g) to remove the plasma and the buffycoat.

Leucocytes were removed by a leucocyte depletion filter (BioR, obtained from fresenius HemoCare, Netherlands) and the red blood cells were lysed by adding two volumes of cold water.

Stroma was removed by tangential flow filtration using a 0.45 µm HVMP filter (obtained from Merck Chemicals B.V./Milipore, Netherlands) and the hemolysate was concentrated to the desired haemoglobin concentration by tangential flow filtration using a 10 kDa Delta T-centracette filter (obtained from Pall, Netherlands)

The haemoglobin was converted to methaemoglobin by adding 0.75 mmol $NaNO_2$ per mmol oxyhaemoglobin.

The 100% methaemoglobin solution was sterilized using 0.2 µm filters (AcroPak200).

Example 3: Preparation of Carboxyhaemoglobin

Carbon monoxide was led through the hemolysate prepared according to example 1 or example 2 to convert the hemoglobin to carboxyhaemoglobin.

The carboxyhaemoglobin was sterilized using 0.2 µm filters (AcroPak200).

Example 4: Preparation of the Liquid CO—OX Control

Oxyhaemoglobin, prepared according to example 1, was filled in one compartment of a container as represented in FIG. 1 (1 mL oxyhaemoglobin per container).

Methemoglobin, prepared according to example 2 was filled in the other compartment of a container as represented in FIG. 1 (1 mL methemoglobin per container).

Before filling, carboxyhaemoglobin, prepared according to example 3 was mixed with the oxyhaemoglobin or the methemoglobin.

By varying in the concentration of the total hemoglobin and by mixing different amounts of carboxyhaemoglobin with oxyhaemoglobin and/or methemoglobin 6 levels were made with different concentrations of total hemoglobin and different fractions of oxyhaemoglobin, methemoglobin and carboxyhaemoglobin.

The liquid CO—OX controls were stored at 2-8° C.

Example 5

After mixing of both compartments of the container the controls were analyzed on a CO-oximeter (ABL800) with the following results:

TABLE 1

| Eurotrol Liquid CO-OX control | | | | |
|---|---|---|---|---|
| Eurotrol Control | tHb g/dL | $O_2Hb$ % | COHb % | MetHb % |
| Level 1 | 18.0 | 93.7 | 6.3 | 2.1 |
| Level 2 | 10.3 | 82.1 | 11.1 | 8.8 |
| Level 3 | 12.3 | 72.6 | 15.2 | 14.0 |
| Level 4 | 13.2 | 57.3 | 21.5 | 22.5 |
| Level 5 | 14.7 | 51.9 | 25.9 | 23.5 |
| Level 6 | 17.2 | 40.7 | 29.2 | 31.0 |

For comparison an existing CO—OX control (QC 253 Full Range CO-Oximeter Control of RNA Medical) was measured.

TABLE 2

| Existing CO-OX controls RNA QC 253 Full Range CO-Oximeter Control | | | | |
|---|---|---|---|---|
| RNA Control | tHb g/dL | $O_2Hb$ % | COHb % | MetHb % |
| Level 1 | 8.1 | 96.6 | 2.5 | 0.3 |
| Level 2 | 13.9 | 83.5 | 15.3 | 0.2 |
| Level 3 | 17.5 | 55.4 | 43.2 | 0.3 |

CONCLUSION

A comparison of the Eurotrol Liquid CO—OX control with the RNA QC 253 Full Range CO-Oximeter Control shows the advantage of the Eurotrol Liquid CO—OX control: each level of the Eurotrol Liquid CO—OX control consists of different percentages of O2Hb, COHb and MetHb, and each different Hb fraction can be present in concentrations in high ranges, low ranges, or middle ranges. For example, MetHb can be present in concentrations ranging from about 2% to about 30%, and O2Hb can be present in concentrations ranging from about 90% to about 40%. In contrast, the values in table 2 show that only the concentrations of O2Hb and COHb are substantial, and that only said concentrations actually show significant absolute variation.

Each level of the RNA QC 253 Full Range CO-Oximeter Control consists of different percentages of O2Hb and COHb but the percentage MetHb is the same (and very low) for all levels.

Example 6: Stability of the Liquid CO—OX Control

Hemolysate was produced according to example 1 and placed at 2-8° C. As a control, hemolysate without a methaemoglobin reductase system present was produced and placed at 2-8° C. At certain time points both samples were measured on a CO-oximeter (ABL800) with the following results:

TABLE 3

| Hemolysate without methaemoglobin reductase | | |
|---|---|---|
| # days at 2-8° C. | O2Hb, % | MetHb, % |
| 0 | 94.4 | 6.9 |
| 11 | 92.5 | 9.3 |
| 28 | 89.6 | 12.1 |

TABLE 4

Stabilized Hemolysate

| # days at 2-8° C. | O2Hb, % | MetHb, % |
|---|---|---|
| 0 | 95.4 | 2.2 |
| 12 | 95.0 | 2.2 |
| 26 | 95.4 | 2.3 |
| 139 | 95.1 | 2.6 |

For the stabilized hemolysate, both the oxyhaemoglobin fraction and the methaemoglobin fraction are stable. In the untreated hemolysate, the oxyhaemoglobin is oxidized to methaemoglobin, so that both fractions vary in time. Oxidation to methaemoglobin already commences during the production process.

Example 7: Reliability of Liquid CO—OX Controls

A number of liquid controls according to example 4 with a tHb of about 13.5 g/dL, an O2Hb fraction of about 61%, a COHb fraction of about 20%, and a MetHb fraction of about 18.5% were prepared. The containers were distributed over a large number of laboratories, where various types of CO-oximeters were installed. The liquid controls were measured and the results are shown in table 5.

TABLE 5

Reliability across labs and devices

| | tHb | | O2Hb | | COHb | | MetHb | |
|---|---|---|---|---|---|---|---|---|
| Peer Group | Labs | Mean(SD) | Labs | Mean(SD) | Labs | Mean(SD) | Labs | Mean(SD) |
| AVOXimeter 1000, 4000 | 116 | 13.54(0.47) | 124 | 60.22(1.12) | 87 | 19.77(1.28) | 63 | 17.52(0.76) |
| IL GEM OPL | 33 | 13.42(0.36) | 38 | 61.01(0.71) | 52 | 19.69(1.11) | 35 | 17.55(0.63) |
| IL Gem Premier 4000 | 68 | 12.35(0.24) | 70 | 62.23(0.7) | 77 | 20.61(0.4) | 65 | 18.11(0.69) |
| Radiometer ABL 80 Co-oximeter | 73 | 13.28(0.31) | 71 | 62.29(0.65) | 93 | 18.79(0.45) | 66 | 20.02(0.47) |
| Radiometer ABL 800 series | 52 | 13.43(0.13) | 51 | 61.05(0.73) | 62 | 19.35(0.32) | 53 | 20.68(0.35) |
| Radiometer ABL 90 | 11 | 13.93(0.41) | 13 | 62.75(0.46) | 16 | 18.89(0.25) | 13 | 19.96(0.52) |
| Roche cobas b 221 | 29 | 12.87(0.08) | 25 | 61.26(0.39) | 38 | 19.84(0.2) | 31 | 18.47(0.33) |
| Siemens 1265 | 14 | 14.21(0.27) | 11 | 61.15(1.57) | 15 | 20.52(0.3) | 12 | 17.98(1.55) |
| Siemens 1245, 1265 | 16 | 14.23(0.26) | 13 | 61.24(1.45) | 17 | 20.53(0.28) | 14 | 17.93(1.49) |
| Siemens RapidPoint 405 | 66 | 14.44(0.17) | 65 | 61.96(0.44) | 75 | 20.22(0.26) | 62 | 17.57(0.3) |
| Siemens RapidPoint 500 | 39 | 14.55(0.16) | 41 | 61.71(0.58) | 47 | 20.36(0.25) | 39 | 17.73(0.49) |
| Siemens RapidPoint 405, 500 | 105 | 14.48(0.17) | 106 | 61.9(0.44) | 122 | 20.28(0.26) | 101 | 17.65(0.44) |
| All Participants | 506 | 13.51(0.75) | 513 | 61.38(1.15) | 570 | 19.76(0.89) | 445 | 18.58(1.35) |

The invention claimed is:

1. A container comprising at least two adjacent compartments, a first compartment of the at least two adjacent compartments comprising a liquid oxyhaemoglobin fraction and a second compartment of the at least two adjacent compartments comprising a liquid methaemoglobin fraction.

2. A container according to claim 1, wherein said at least two compartments can be brought in fluid communication with each other.

3. A container according to claim 1, wherein said at least two compartments are part of an assembly arranged for separately storing said haemoglobin fractions.

4. A container according to claim 1, wherein an additional carboxyhaemoglobin fraction is present in the first compartment or in the second compartment.

5. A container according to claim 4, wherein the oxyhaemoglobin, the methaemoglobin or the carboxyhaemoglobin are derived from mammalian blood.

6. A container according to claim 5, wherein the mammalian blood is bovine blood or human blood.

7. A container according to claim 1, wherein other haemoglobin fractions are present either in the first and/or in the second compartment.

8. A container according to claim 1, wherein the first compartment further comprises methaemoglobin reductase.

9. A container according to claim 1, wherein the at least two compartments are part of an assembly arranged for separately storing the haemoglobin fractions, the assembly further comprising a mixing arrangement providing a communication channel between the at least two compartments for mixing the haemoglobin fractions directly prior to use.

10. A container according to claim 1, wherein an additional analyte is present in the first compartment or second compartment of said container.

11. A container according to claim 1, wherein bilirubine is present in the first compartment or the second compartment of said container.

12. A kit for determining the reliability of a CO-oximetry device, the kit comprising (i) at least one container as defined in claim 1, and (ii) instructions for mixing the haemoglobin fractions contained within the container to obtain one or more control samples, and for measuring the concentration of a haemoglobin fraction present using said device.

13. A method for determining the reliability of a CO-oximetry device, comprising the following successive steps:
 a) mixing haemoglobin fractions present in a container as defined in claim 1 to obtain one control sample having defined concentrations of haemoglobin fractions;
 b) measuring, by means of the device, the concentration of a haemoglobin fraction present in the control sample of step a);

c) determining the reliability of the device on the basis of the difference between (i) the known concentrations of the haemoglobin fractions of the sample obtained at the end of step a) and (ii) the result of the measurement of the measurement of step b).

14. The container according to claim 1, wherein the oxyhaemoglobin is stabilized.

15. A container according to claim 1, wherein at least one of the oxyhaemoglobin or the methaemoglobin are derived from mammalian blood.

* * * * *